(12) United States Patent
Cox et al.

(10) Patent No.: US 10,722,700 B2
(45) Date of Patent: *Jul. 28, 2020

(54) DISTAL VALVE FOR A CATHETER

(71) Applicant: C. R. Bard, Inc., Murray Hill, NJ (US)

(72) Inventors: Jeremy B. Cox, Salt Lake City, UT (US); Daniel B. Blanchard, Bountiful, UT (US); Mark A. Christensen, Salt Lake City, UT (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 92 days.

This patent is subject to a terminal disclaimer.

(21) Appl. No.: 15/785,774

(22) Filed: Oct. 17, 2017

(65) Prior Publication Data
US 2018/0036525 A1 Feb. 8, 2018

Related U.S. Application Data

(62) Division of application No. 13/857,940, filed on Apr. 5, 2013, now Pat. No. 9,827,411.
(Continued)

(51) Int. Cl.
*A61M 39/22* (2006.01)
*A61M 25/00* (2006.01)
*A61M 39/24* (2006.01)

(52) U.S. Cl.
CPC ........ *A61M 39/22* (2013.01); *A61M 25/0009* (2013.01); *A61M 25/0015* (2013.01);
(Continued)

(58) Field of Classification Search
CPC .............. A61M 25/0015; A61M 39/22; A61M 25/0075; A61M 25/0009;
(Continued)

(56) References Cited

U.S. PATENT DOCUMENTS

| 4,549,879 A | 10/1985 | Groshong et al. |
| 4,671,796 A | 6/1987 | Groshong et al. |

(Continued)

FOREIGN PATENT DOCUMENTS

| CN | 1187598 A | 7/1998 |
| EP | 0109657 A1 | 5/1984 |

(Continued)

OTHER PUBLICATIONS

CA 2864734 filed Aug. 14, 2014 Office Action dated Jan. 7, 2019.
(Continued)

*Primary Examiner* — Theodore J Stigell
(74) *Attorney, Agent, or Firm* — Rutan & Tucker LLP

(57) ABSTRACT

A bi-directional valve assembly, including valves for use in closed-ended catheters or other elongate tubular devices, is disclosed. In one embodiment, a catheter assembly for insertion into a body of a patient is disclosed and comprises an elongate catheter tube including an outer wall that at least partially defines at least one lumen that extends between a proximal end and a closed distal end thereof. The catheter tube includes a valve assembly that in turn includes a linear slit valve defined through the outer wall of a distal segment of the catheter tube, and a deformation region. The deformation region includes a compliant segment disposed in the outer wall of the catheter tube and a thinned portion of the outer wall. The compliant segment and thinned portion of the deformation region cooperate to preferentially deform the outer wall and open the slit valve during aspiration through the catheter tube.

14 Claims, 7 Drawing Sheets

Related U.S. Application Data

(60) Provisional application No. 61/621,276, filed on Apr. 6, 2012.

(52) U.S. Cl.
CPC ..... *A61M 25/0075* (2013.01); *A61M 25/0068* (2013.01); *A61M 2025/0078* (2013.01); *A61M 2039/242* (2013.01); *A61M 2039/2406* (2013.01); *A61M 2039/2433* (2013.01); *Y10T 29/49405* (2015.01)

(58) Field of Classification Search
CPC .. A61M 2025/0078; A61M 2039/2406; A61M 2039/242; A61M 2039/2433
See application file for complete search history.

(56) References Cited

U.S. PATENT DOCUMENTS

| | | |
|---|---|---|
| 4,701,166 A | 10/1987 | Groshong et al. |
| 4,801,297 A | 1/1989 | Mueller |
| 4,973,319 A | 11/1990 | Melsky |
| 4,995,863 A | 2/1991 | Nichols et al. |
| 5,030,210 A | 7/1991 | Alchas |
| 5,112,301 A | 5/1992 | Fenton, Jr. et al. |
| 5,147,332 A | 9/1992 | Moorehead |
| 5,261,885 A | 11/1993 | Lui |
| 5,304,155 A | 4/1994 | Lui |
| 5,312,363 A | 5/1994 | Ryan et al. |
| 5,474,099 A | 12/1995 | Boehmer et al. |
| 5,522,807 A | 6/1996 | Luther |
| 5,554,136 A | 9/1996 | Luther |
| 5,785,694 A | 7/1998 | Cohen et al. |
| 5,807,349 A | 9/1998 | Person et al. |
| 5,807,356 A | 9/1998 | Finch, Jr. et al. |
| 5,857,464 A | 1/1999 | Desai |
| 5,895,376 A | 4/1999 | Schwartz et al. |
| 5,928,203 A * | 7/1999 | Davey ............... A61M 25/0075 137/848 |
| 5,984,903 A | 11/1999 | Nadal |
| 6,052,612 A | 4/2000 | Desai |
| 6,592,544 B1 | 7/2003 | Mooney et al. |
| 6,663,596 B2 | 12/2003 | Griego et al. |
| 6,723,075 B2 | 4/2004 | Davey et al. |
| 6,783,522 B2 | 8/2004 | Fischell |
| 6,887,270 B2 | 5/2005 | Miller et al. |
| 6,908,449 B2 | 6/2005 | Willis et al. |
| 7,211,074 B2 | 5/2007 | Sansoucy |
| 7,413,564 B2 | 8/2008 | Morris et al. |
| 7,491,192 B2 | 2/2009 | DiFiore |
| 8,057,439 B2 | 11/2011 | Di Fiore |
| 8,083,728 B2 | 12/2011 | Rome |
| 8,864,724 B2 | 10/2014 | Onuma |
| 9,827,411 B2 * | 11/2017 | Cox ..................... A61M 39/22 |
| 2002/0156430 A1 * | 10/2002 | Haarala ............. A61M 25/0075 604/247 |
| 2004/0158208 A1 | 8/2004 | Hiejima |
| 2004/0176743 A1 | 9/2004 | Morris et al. |
| 2004/0193118 A1 | 9/2004 | Bergeron |
| 2005/0038413 A1 | 2/2005 | Sansoucy |
| 2005/0043703 A1 | 2/2005 | Nordgren |
| 2005/0049555 A1 | 3/2005 | Moorehead et al. |
| 2005/0113805 A1 | 5/2005 | Devellian et al. |
| 2005/0283122 A1 | 12/2005 | Nordgren |
| 2006/0149191 A1 | 7/2006 | DiFiore |
| 2006/0253084 A1 | 11/2006 | Nordgren |
| 2007/0225678 A1 * | 9/2007 | Lui ................... A61M 25/0023 604/523 |
| 2009/0312718 A1 * | 12/2009 | Onuma ............. A61M 25/0075 604/246 |
| 2011/0054415 A1 | 3/2011 | Onuma et al. |
| 2011/0082444 A1 | 4/2011 | Mayback et al. |
| 2011/0160663 A1 * | 6/2011 | Stout ................. A61M 25/0009 604/122 |
| 2011/0313354 A1 | 12/2011 | Hennessy |
| 2013/0267912 A1 | 10/2013 | Cox et al. |

FOREIGN PATENT DOCUMENTS

| | | |
|---|---|---|
| EP | 2 289 590 A1 | 3/2011 |
| EP | 2 497 518 A1 | 9/2012 |
| JP | 2011-050420 A | 3/2011 |

OTHER PUBLICATIONS

EP 13773013.1 filed Apr. 5, 2013 Office Action dated May 22, 2018.
EP 19162527.6 filed Mar. 13, 2019 Extended European Search Report dated Apr. 12, 2019.
CN 201380019003.3 filed Oct. 8, 2014 First Office Action dated Jan. 7, 2016.
CN 201380019003.3 filed Oct. 8, 2014 Office Action dated Aug. 5, 2016.
CO 14.244.159 filed Nov. 5, 2014 First Office Action dated Apr. 11, 2016.
EP 13773013.1 filed Apr. 5, 2013 Extended European Search Report dated Oct. 13, 2015.
EP 13773013.1 filed Apr. 5, 2013 Response to Extended European Search Report dated Jul. 13, 2016.
JP 2015-504756 filed Oct. 3, 2014 Office Action dated Dec. 27, 2016.
MX/a/2014/011885 filed Oct. 1, 2014 Office Action dated Jun. 22, 2017.
MX/a/2014/011885 filed Oct. 1, 2014 Office Action dated Nov. 17, 2016.
PCT/US13/35511 filed Apr. 5, 2013 International Search Report and Written Opinion dated Jun. 25, 2013.
U.S. Appl. No. 13/857,940, filed Apr. 5, 2013 Notice of Allowance dated Mar. 3, 2017.
U.S. Appl. No. 13/857,940, filed Apr. 5, 2013, Final Office Action dated Nov. 13, 2015.
U.S. Appl. No. 13/857,940, filed Apr. 5, 2013, Non-Final Office Action dated Jul. 24, 2015.
U.S. Appl. No. 13/857,940, filed Apr. 5, 2013, Non-Final Office Action dated Nov. 28, 2016.
CN 201710152961.8 filed Mar. 15, 2017 Office Action dated Apr. 16, 2019.

* cited by examiner

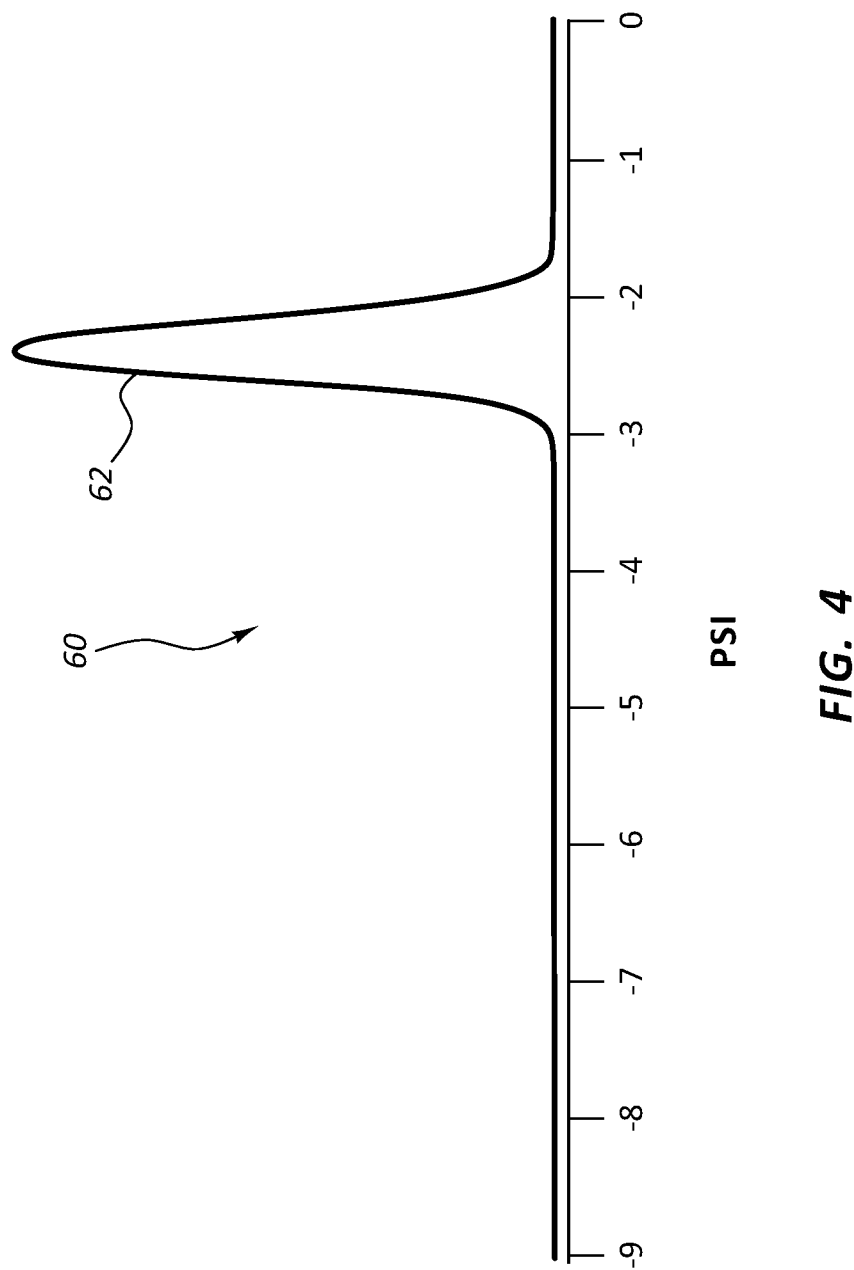

DISTAL VALVE FOR A CATHETER

CROSS-REFERENCE TO RELATED APPLICATIONS

This application is a division of U.S. patent application Ser. No. 13/857,940, filed Apr. 5, 2013, now U.S. Pat. No. 9,827,411, which claims the benefit of U.S. Provisional Patent Application No. 61/621,276, filed Apr. 6, 2012, and titled "Distal Valve for a Catheter," each of which is incorporated herein by reference in its entirety.

BRIEF SUMMARY

Briefly summarized, embodiments of the present invention are directed to a valve assembly, including valves for use in closed-ended catheters or other elongate tubular devices. The valve is employed to provide a selectively openable, bi-directional barrier between the interior and the exterior of the catheter. When the valve is at rest, the valve is closed so as to prevent the passage of air or fluids. When a sufficient aspiration or infusion force is applied, the valve opens either inwardly or outwardly to permit the passage of fluids therethrough. Once the force is removed, the valve returns to its closed position. As will be seen, the valve assembly is configured so as to provide reliable, low friction opening of the valve while also preventing the unintended catching of valve surfaces during operation.

In one embodiment, a catheter assembly for insertion into a body of a patient is disclosed and comprises an elongate catheter tube including an outer wall that at least partially defines at least one lumen that extends between a proximal end and a closed distal end thereof. The catheter tube includes a valve assembly that in turn includes a linear slit valve defined through the outer wall of a distal segment of the catheter tube, and a deformation region disposed on the distal segment. The deformation region includes a compliant segment disposed in the outer wall of the catheter tube and a thinned portion of the outer wall. The compliant segment and thinned portion of the deformation region cooperate to preferentially deform the outer wall of the catheter tube when an aspiration force is present in the at least one lumen so as to assist in opening the slit valve.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 4 is a graph showing aspects of operation of the distal valve of FIGS. 3A-3D according to one embodiment;

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present invention are generally directed to valve assemblies, including valves for use in closed-ended catheters or other elongate tubular devices. The valve is employed to provide a selectively openable, bi-directional barrier between the interior and the exterior of the catheter. When the valve is at rest, the valve is closed so as to prevent the passage of air or fluids. When a sufficient aspiration or infusion force is applied, the valve opens either inwardly or outwardly to permit the passage of fluids therethrough. Once the force is removed, the valve returns to its closed position. As will be seen, the valve assembly is configured so as to provide reliable, low friction opening of the valve while also preventing the unintended catching of valve surfaces during operation.

Figure 1:
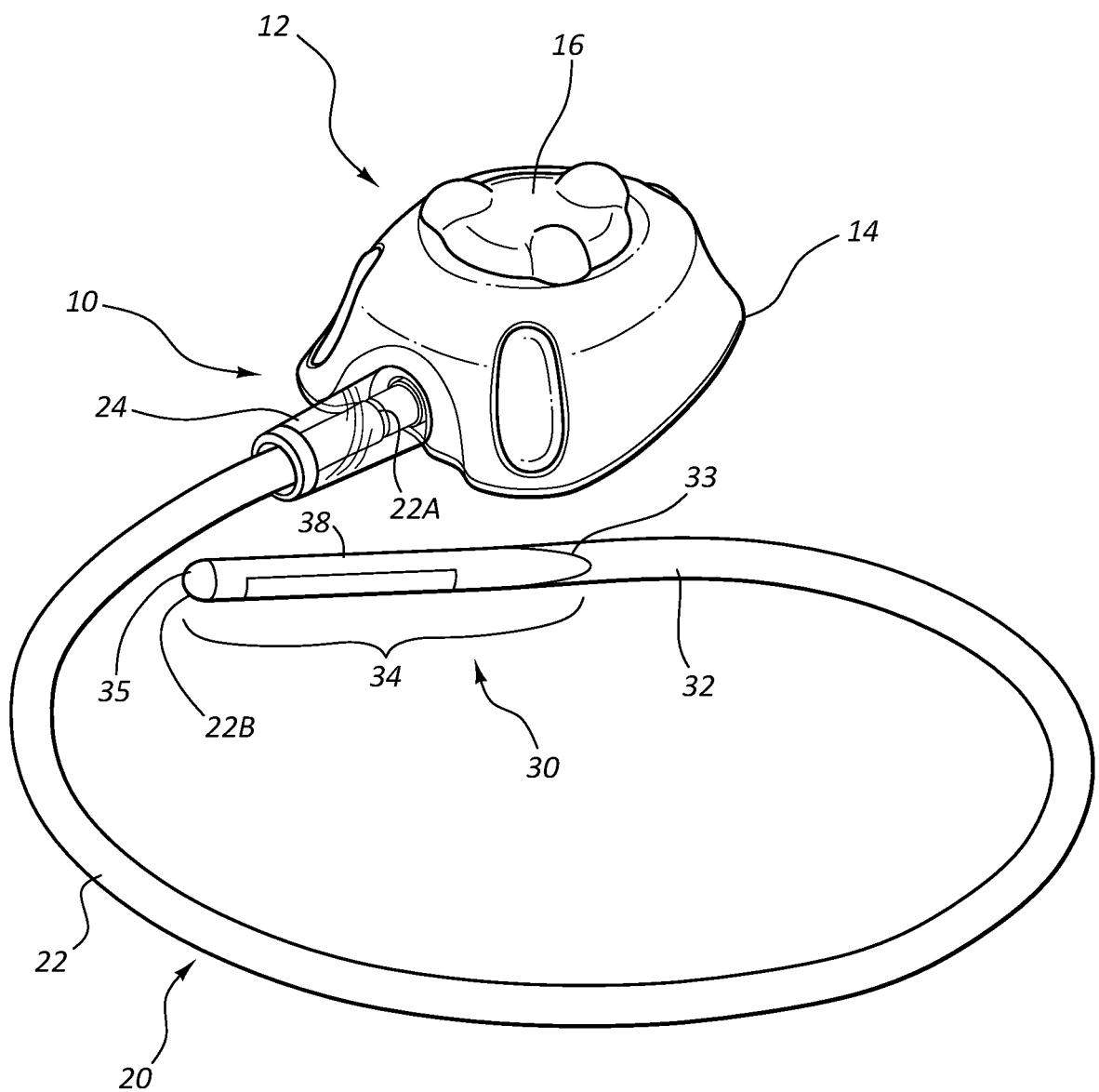
FIG. 1 is a perspective view of an implantable access port and attached catheter assembly, which serve as one example environment where embodiments of the present disclosure can be practiced.

FIG. 1 shows a port/catheter assembly ("assembly"), generally designated at 10, as an example of an environment where the valve assembly can be employed, according to one embodiment. As shown, the assembly 10 includes an implantable access port 12 and attached catheter 20 configured for implantation into a body of a patient so as to provide fluid access to the vasculature of the patient. The port 12 includes a body 14 and a needle-penetrable septum 16 that covers a fluid reservoir defined by the body. The catheter 20 includes an elongate and flexible, or compliant, catheter tube 22 that defines one or more lumens 43 (FIG. 2C) extending from a proximal end 22A to a distal end 22B of the tube. The proximal end 22A of the catheter tube 22 fits over a stem extending from the port body 14 and is secured thereto via a connector 24.

A valve assembly 30 according to one embodiment is included at a distal segment 34 of the catheter tube 22. The distal segment 34 is shown as a discrete piece attached via adhesive, overmolding, or other suitable bonding to a proximal portion 32 of the catheter tube via a skived interface 33, though in other embodiments the distal segment can be integrally formed with the proximal tube portion. The distal end 22B of the catheter tube 20 is closed, such as via a plug 35 or other suitable closure scheme.

Figure 2A:
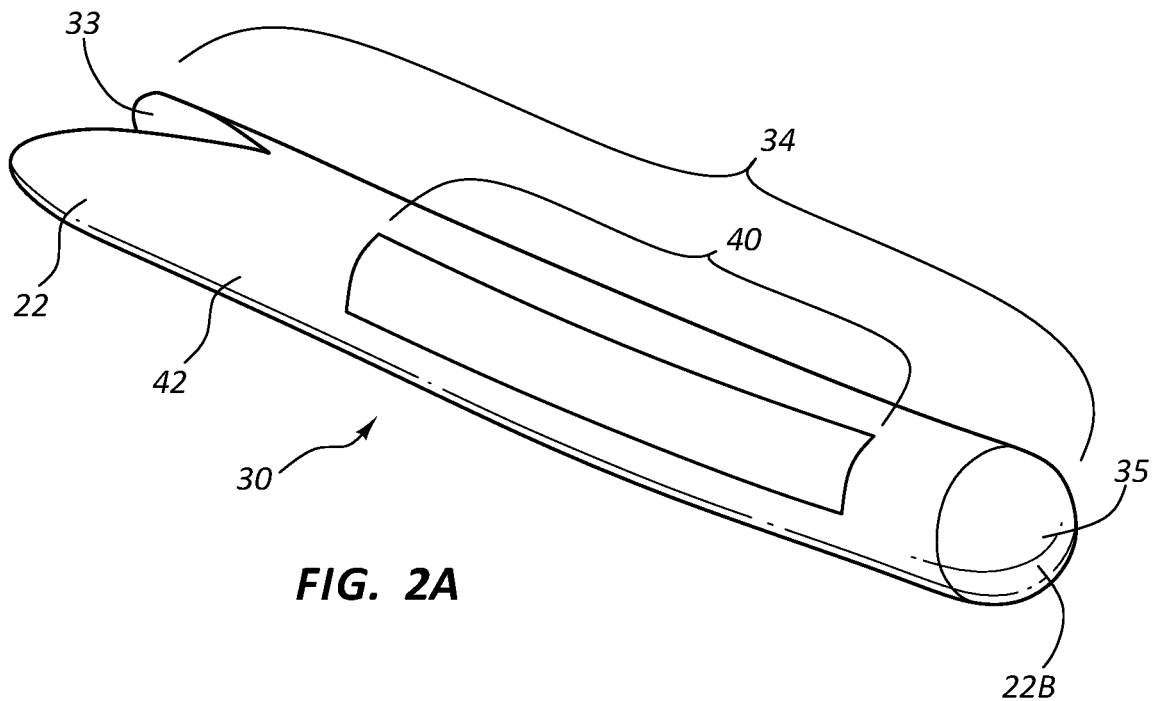
FIGS. 2A-2C are various views of a distal segment of a catheter tube in accordance with one embodiment.
Figure 2B:
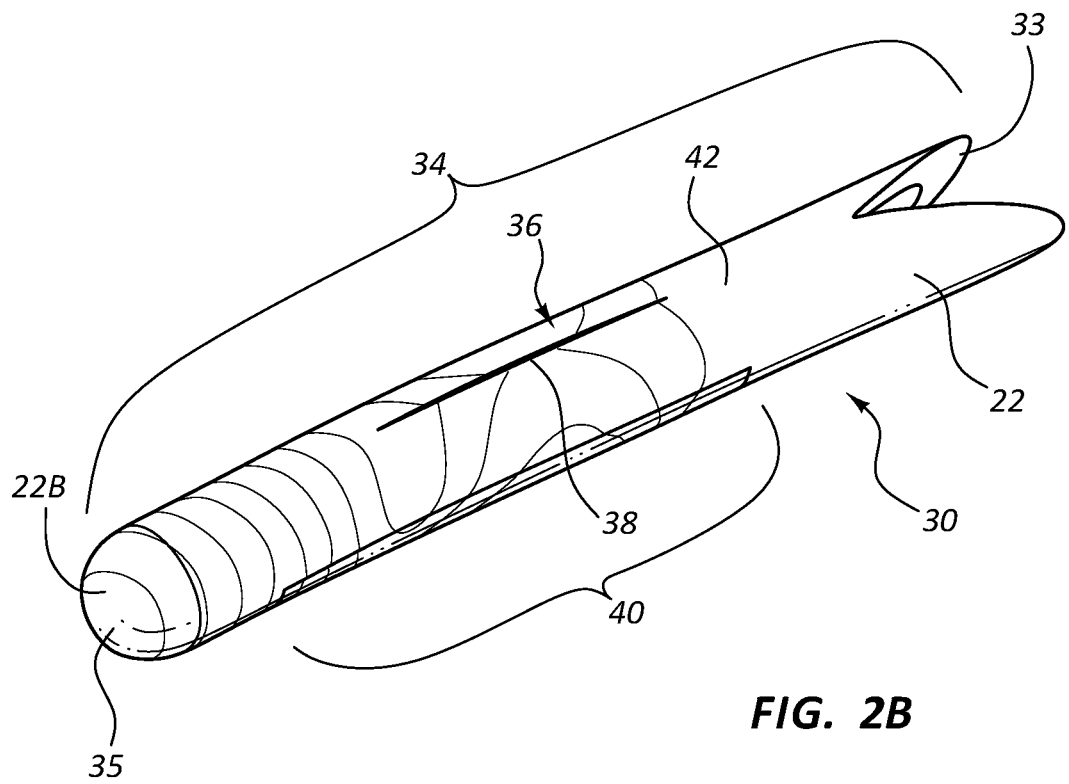
Figure 2C:
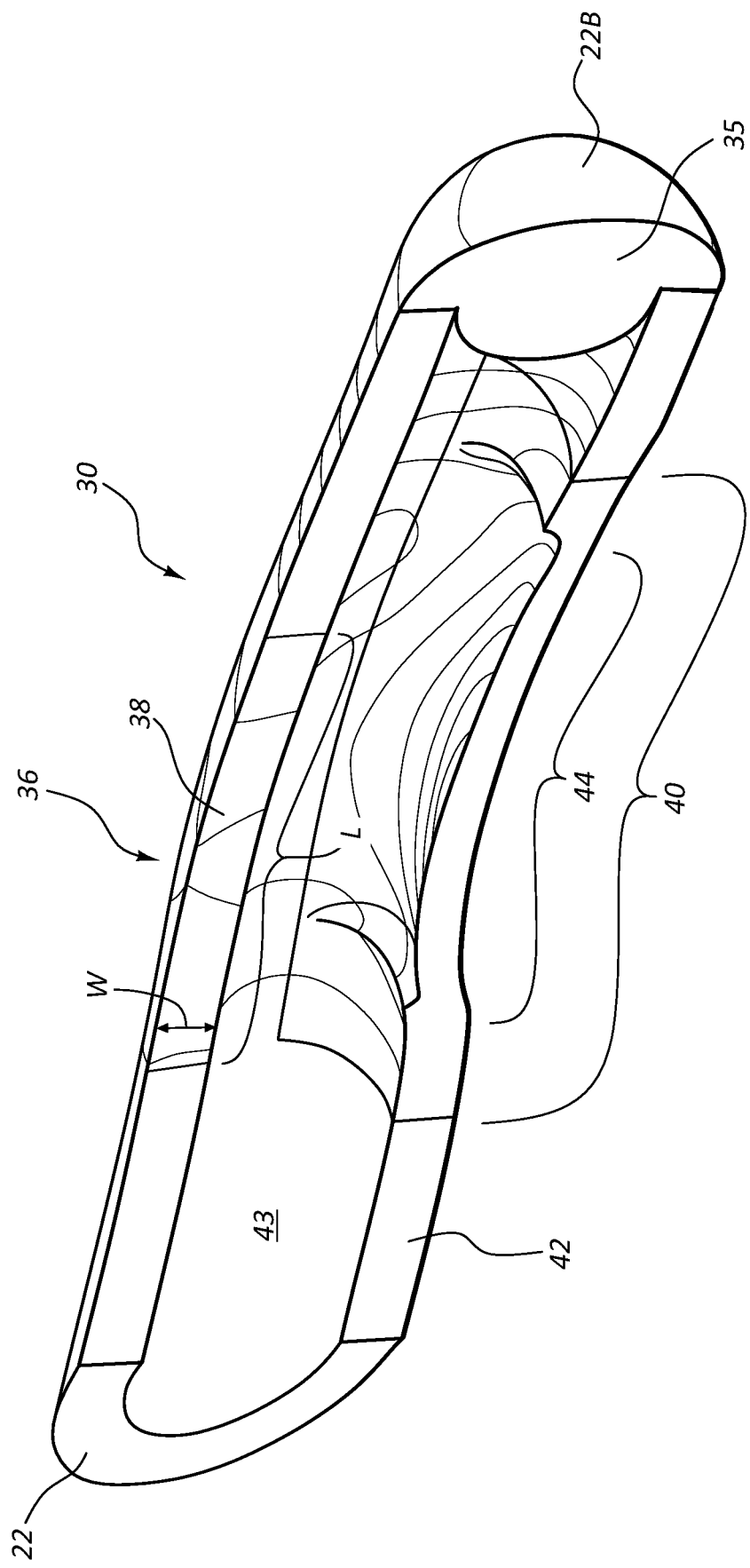

FIGS. 2A-2C show further details of the valve assembly 30 according to one embodiment. A slit valve 36 is shown, including a longitudinally defined slit 38 that extends through an outer wall 42 defining the catheter tube 20 to provide valved access to the lumen 43. The slit valve 36 is configured so as to deflect outwardly when a sufficient positive pressure is present in the lumen 43 such that fluids can pass from the lumen into the vessel or other location of the patient body in which the catheter is disposed. Passage of fluids from the catheter tube lumen is also referred to herein as "infusion." The slit valve 36 is further configured to deflect inwardly when a sufficient negative pressure is present in the lumen 43 such that fluids can be drawn into the lumen, also referred to herein as "aspiration."

As best seen in FIG. 2C, the slit valve 36 includes a longitudinal length L and a width W. In one embodiment, a ratio of length L to width W of the slit valve 36 has a value of about 10:1 so as to provide sufficient restorative force to return to its undeflected, or at-rest, position shown in FIG. 2B. Of course, other slit length-to-width ratios can be employed, including within the range of from about 8:1 to about 15:1, in one embodiment.

It is noted here that a slit valve is readily deflectable to provide fluid infusion into the vessel as sufficient positive pressure is readily producible within the catheter tube lumen 43 via connection of the catheter with pressure-producing external apparatus. Deflection of the slit valve 36 to produce aspiration into the catheter tube lumen 43 under an infusion force, however, is relatively more difficult as negative pressures only up to −1 atmosphere ("atm") are possible. As such, any slit valve solution should ensure adequate and reliable valve opening under negative pressure, i.e., under aspiration force, within the catheter tube lumen. Correspondingly, the slit valve should also be configured to close adequately and securely when no slit opening force, i.e., aspiration force or infusion force, is present.

In accordance with one embodiment, a deformation region is included in the valve assembly 30 so as to assist in deflection of the slit valve 36 during aspiration. The deformation region preferentially deforms when a sufficient negative pressure is present in the lumen 43 of the catheter tube 22, such as an aspiration force that is present when the catheter 20 is being employed for aspiration of fluids therethrough. As seen in FIGS. 2A-2C, the deformation region in the present embodiment is implemented as a compliant segment 40 that includes a segment of material forming the outer wall 42 that is softer in durometer, or hardness, relative to the surrounding material of which the remainder of the distal segment outer wall is composed. Generally, a durometer rating for the compliant segment material at about 10 to about 20 less than that of the surrounding outer wall material is sufficient to provide the desired preferential deformation of the compliant segment to open the slit valve, as described further below.

In light of the above, in the present embodiment the compliant segment material includes silicone of durometer rating about 50 while the surrounding distal segment outer wall includes silicone of about 70. The proximal tube portion 32 also includes silicone and possesses a durometer of about 50, though this may vary. It is appreciated that the specific durometer ratings of the aforementioned components can vary according to application, material used, amount of desired deformation/valve opening, etc. Further, materials other than silicone can be used in the outer wall of the valve assemblies/distal segments described herein. Generally, the material used for catheter assemblies for patient insertion should be biocompatible, possess an acceptable durometer range, low tendency for creep, be able to bond with other catheter tube portions if necessary, and be able to retain the desired physical form of the catheter tube such that the catheter can operate as intended. Examples of suitable materials that can be employed include silicone, polyurethane, polyurethane/silicone mixtures, polycarbonate/polyurethane copolymers, etc. In the case of polyurethane, a coating may be applied to the faces of the slit valve to prevent knitting together of the slit faces. Such a coating can include parylene, for instance.

The length of the compliant segment 40 is slightly larger than that of the slit 38 of the slit valve 36, though this and the other dimensions of the compliant segment can be varied from what is shown and described herein. The circumferential breadth of the compliant segment 40 is shown in FIGS. 2C and 3A to extend in the present embodiment about a quarter of the circumference of the catheter tube when viewed cross-sectionally (FIG. 3A).

The compliant segment 40 is positioned in a spaced-apart relationship with respect to the slit valve 36 so as to assist in opening of the slit valve when the compliant segment preferentially deforms under an aspiration force as explained further below. As seen in FIGS. 2C and 3A, the position of the compliant segment 40 extends from about 90 degrees to about 180 degrees circumferentially away from the slit valve 36, assuming the slit valve is positioned a circumferential position of 0 degrees. Again, the particular position of the compliant segment can vary.

Figure 3A:
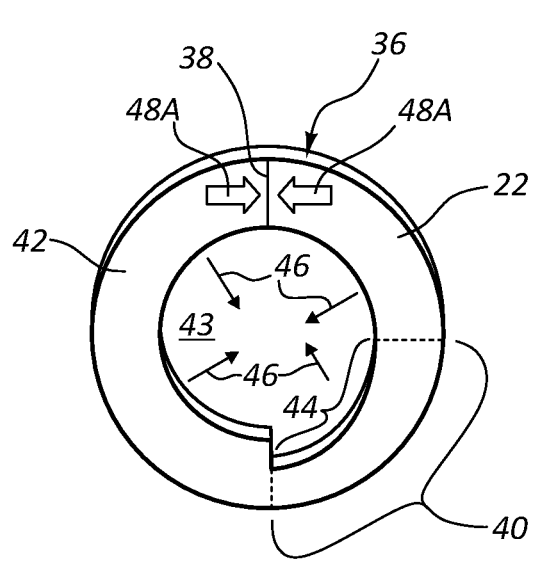
FIGS. 3A-3D show various cross sectional views of the catheter tube distal segment of FIGS. 2A-2C showing operation of a distal valve in accordance with one embodiment.

As best illustrated in FIGS. 2C and 3A, the deformation region in the present embodiment is further implemented as a thinned portion 44 of the outer wall 42 of the catheter tube 22. As shown, the thinned portion 44 is tapered in its thickness in the present embodiment, with it being thinnest at a position substantially opposite the slit valve 36, i.e., about 180 degrees circumferentially away from the slit valve. From this thinnest point, the thinned portion 44 tapers up in thickness to the full thickness of the outer wall 42 near about 90 degrees circumferentially away from the slit valve 36. FIG. 2C shows that the longitudinal extent of the thinned portion 44 is shorter than and approximately centered within the length of the compliant segment 40.

Thus the deformation region, including the compliant segment 40 and the thinned portion 44, is positioned in a circumferentially offset configuration with respect to the slit valve 36. This offset configuration enhances the desired preferential deformation of the catheter tube outer wall during aspiration, as will be described further below. As before, note that the length, circumferential extent, tapering, position, and other aspects of the thinned portion can vary from is shown and described herein. For instance, in one embodiment, the thinned portion is not tapered but is uniformly thin. In another embodiment, the slit valve can be disposed within the thinned portion, compliant segment, or both. These and other modifications are therefore contemplated.

In the illustrated embodiment, the length of the slit 38 is about 0.250 inch, the length of the compliant segment 40 is about 0.5620 inch, the length of the thinned portion 44 is about 0.290 inch, the minimum thickness of the thinned portion is about 0.009 inch, and the thickness of the un-thinned outer wall 42 is about 0.019 inch. These dimensions can be altered in other embodiments.

FIGS. 3A-3D depict various details regarding operation of the valve assembly 30, in particular, opening of the slit valve 36 during aspiration of fluids from outside of the catheter tube 22 to within the lumen 43 thereof. Such aspiration is used, for example, to remove blood or other fluids from the patient's body via the catheter 20/port 10. FIG. 3A shows that when an aspiration force—indicated by aspiration force arrows 46—is present within the catheter tube lumen 43, a resultant force is produced in the outer wall 42 of the catheter tube 22. As shown in FIG. 3A this force, indicated by force arrows 48A, works to prevent opening of the slit 38 of the slit valve 36.

Figure 3B:
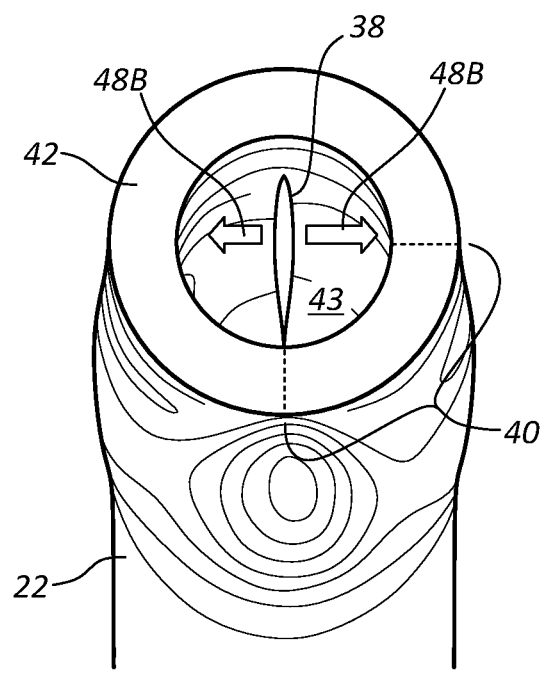

FIG. 3B shows that, because of the inclusion of the deformation region in the catheter tube outer wall 42, including the compliant segment 40 and the thinned portion 44, preferential deformation of the outer wall by the aspiration force occurs proximate the deformation region, as seen on the bottom of the catheter tube in FIG. 3.

Figure 3C:
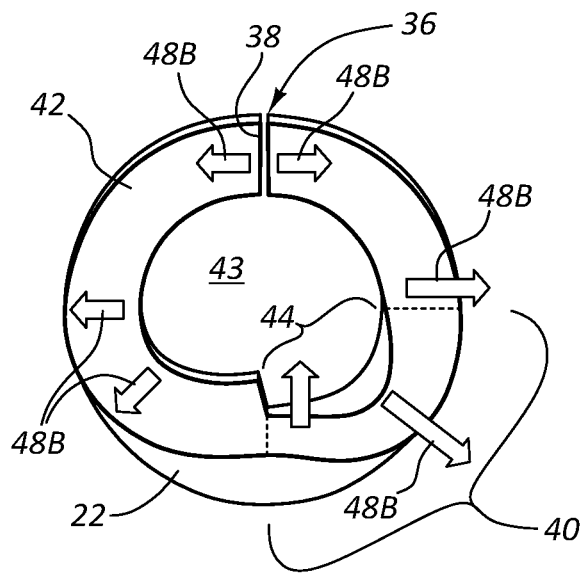

The preferential deformation of the outer wall 42 of FIG. 3B is shown in greater detail in FIG. 3C. In particular, the offset position of the compliant segment 40 and thinned portion 44 of the deformation region causes the outer wall proximate the deformation region to preferentially deform, or buckle, before other wall portions, due to the relatively weaker strength of the wall in this region as a result of its thinness and relative softness. This buckling alters the forces present in the outer wall as shown by force arrows 48B. Specifically, the force arrows 48B proximate the slit 36 show that the outer wall force at the slit facilitate its opening.

Figure 3D:
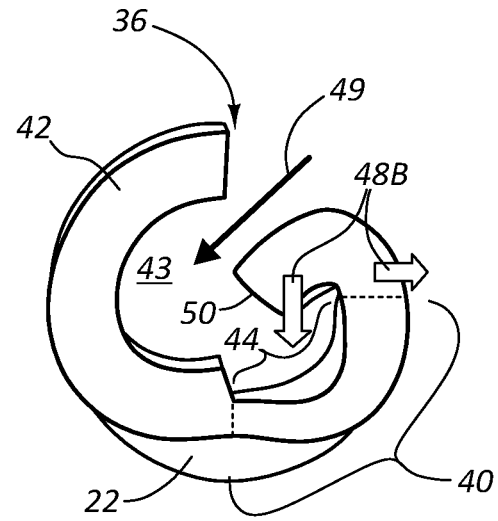

Further buckling of the deformation region soon causes sufficient opening of the slit valve 36 that a face 50 of the slit 36 will deflect, completing opening of the slit valve and enabling fluid to enter the catheter tube lumen 43 as part of an aspiration procedure. Force arrows 48B in FIG. 3D show how the outer forces direct the slit face deflection. Once the aspiration force is removed, the slit valve resiliently repositions itself as shown in FIG. 3A.

FIG. 4 shows a graph 60 including a curve 62 showing the negative (aspiration force) pressures at which the slit valve 36 of the valve assembly 30 of FIGS. 2A-3D opens in one embodiment. As shown, the slit valve 36 is configured to reliably open at between about −2 and −3 psi. As already mentioned, the valve assembly and deformation region can be configured so as to modify the pressure(s) at which the slit valve opens, or other aspects of valve operation. For instance, the magnitude of the thinned portion, length and position of the slit valve or thinned portion, etc. can be modified to adjust the pressure at which the slit valve opens.

In one embodiment, the catheter tube, valve assembly, and deformation region described above can be formed in one embodiment by first forming the proximal tube portion 32 (FIG. 1) of the catheter tube by any one of suitable processes, including extrusion, molding, etc. The distal end of the proximal tube portion 32 is skived to define the skived interface 33, then placed in a mold, where the distal segment 34 of the catheter tube 22 is overmolded on to the proximal tube portion.

Note that a core pin is inserted into the tube lumen prior to the above overmolding so that the volume of the catheter tube outer wall 42 where the compliant segment 40 is to be disposed is occupied by a portion of the core pin. A subsequent overmolding with the core pin removed is then performed to add the relatively softer compliant segment 40 and thinned portion 44. A temporary clocking feature extending from the distal end of the completed catheter tube 22 is also molded via this subsequent overmolding to enable the manufacturer to determine proper placement of the slit 38 of the slit valve 36, in one embodiment. The slit 38 is then defined through the catheter tube outer wall 42. The clocking feature is then removed from the distal end and the plug 35 attached to the catheter tube distal end 22B to close the end thereof. Note that the clocking feature can take one of many forms. Note that in one embodiment, the plug 35 can be attached prior to cutting the slit 38. Note also that other or additional steps can be added to the above manufacturing process; as such, the above discussion is not meant to be limiting in any way.

Notwithstanding the above discussion, note that the deformation region in one embodiment can include only one of either the compliant segment or the thinned region while still enabling preferential deformation of the catheter tube outer wall to facilitate opening of the slit valve. Also, the deformation region can include other aspects in addition to one or both of the compliant segment and the thinned portion in order to facilitate slit valve opening.

Note also that, while it is described above in connection with medical catheters, the valve assemblies and deformation regions described herein can be employed in other types of catheters and elongate tubular devices. Also, though shown proximate the distal catheter end, the valve assembly and deformation region can be disposed at other longitudinal locations along the catheter tube.

Figure 5A:
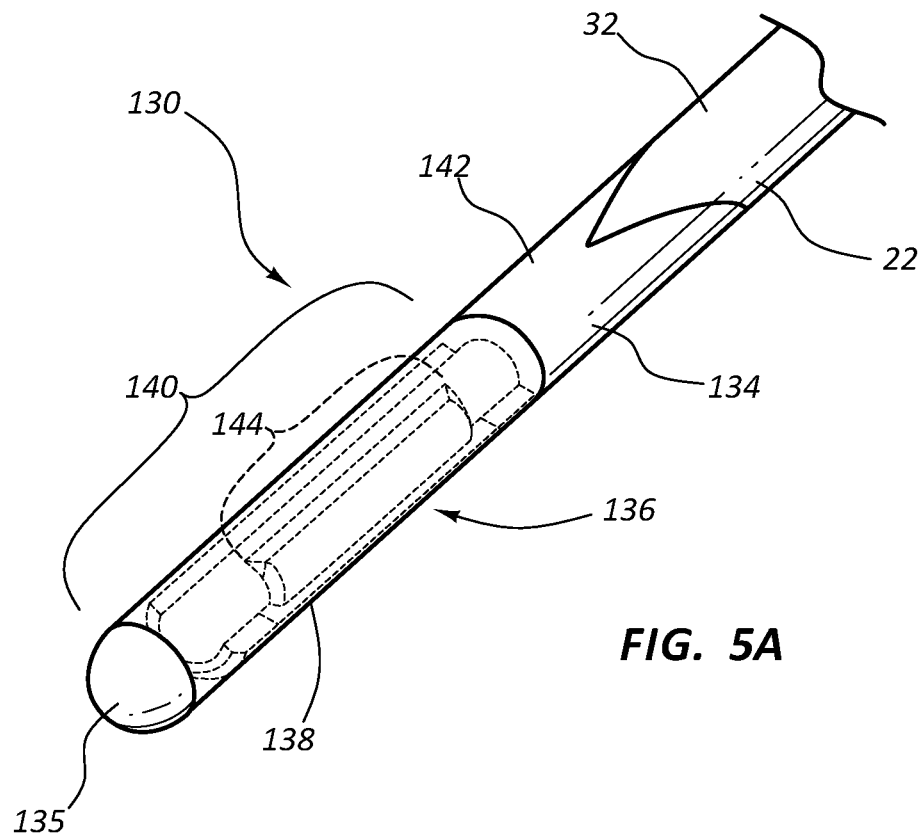
FIGS. 5A-5C show various views of a catheter tube distal segment according to one embodiment.
Figure 5B:
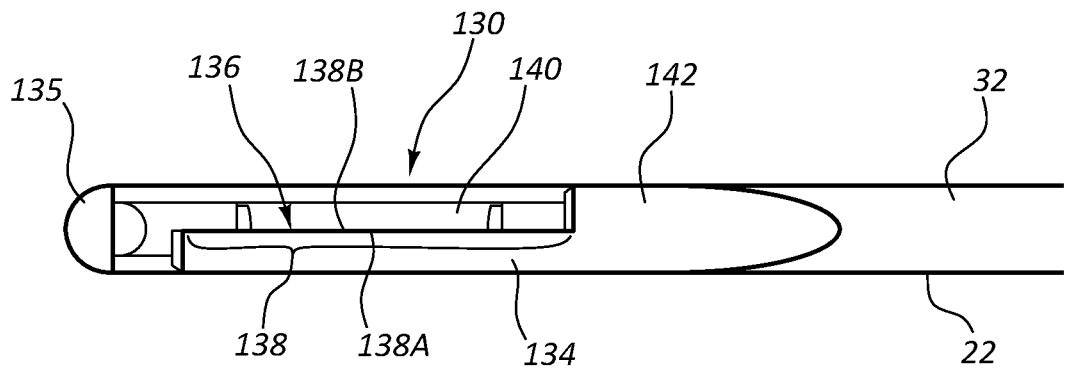
Figure 5C:
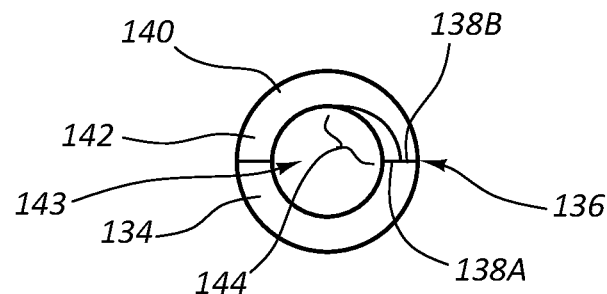

FIGS. 5A-5C show various details of a valve assembly 130 including a deformation region according to another embodiment. As before, the valve assembly 130 is included on a distal portion of the catheter tube 22. In the present embodiment, the valve assembly 130 includes a distal support segment 134 that includes a relatively hard durometer material, such as silicone of durometer of about 70, for instance. As best seen in FIG. 5B, the distal support segment 134 extends from the skived distal end of the proximal tube portion 32 of the catheter tube 22 to a predetermined distance away from the distal end of the catheter tube in a stepped configuration. In another embodiment, the distal support segment can be integrally formed with the proximal tube portion 32.

As shown, the deformation region in the present embodiment is implemented as both a compliant segment 140 and a corresponding thinned portion 144 of the catheter tube outer wall 142. The compliant segment 140 includes a relatively soft durometer material with respect to the durometer of the material of which the distal support segment 134 is composed. In the present embodiment, silicone of durometer of about 50 is used for the compliant segment 140. The compliant segment 140 extends distally in a stepped configuration corresponding to the stepped configuration of the distal support segment 134 so as to complete the outer wall 142 and lumen of the distal portion of the catheter tube 22. As before, a plug 135 or other suitable closure is included to close the distal end of the catheter tube 22. Note that the distal support segment 134 and compliant segment 140 can be formed via successive core pin-assisted injection molding procedures as before, including overmolding and/or rapid injection molding, or by other suitable processes, in one embodiment. Note also that, though in the present embodiment the durometer ratings of the material used for the distal support segment 134 (durometer about 70) and the compliant segment 140 (durometer about 50) differ by about 20, in other embodiments the durometer ratings differ by more or less, such as from about 10 to about 30, in one embodiment. Further note that the catheter tube 22 in the present embodiment includes a relatively softer durometer as compared to the durometer of the distal support segment 134 so as to enable the catheter tube 22 to maneuver relatively easily through the patient vasculature during insertion. It is also appreciated that, in one embodiment, the catheter tube itself can include a durometer that enables it to serve as the distal support segment thus negating the need for a separate distal support segment to be attached to the catheter tube.

The distal support segment 134 defines a first face 138A of a slit 138, while the compliant segment 140 defines a second face 138B of the slit to define a slit valve 138. In one embodiment the length of the slit 138 is about 0.27 inch, but the length can vary according to desire or need.

The first face 138A, second face 138B, or both faces of the slit 138 can include a low friction coating or other substance to prevent sticking together of the faces. In the present embodiment, a polymer coating, such as parylene, is included on the first face 138A of the slit 138, which is defined by the distal support segment 134. Such a coating can be applied via vapor deposition or other suitable process. In another embodiment a coating including silicone with a fluorine additive can be applied to the face(s) 138A/B. In yet another embodiment, a self-lubricating silicone can be used to form the distal support segment 134, the compliant segment 140, or both components, thus providing a self-lubricating solution for the valve slit to prevent valve hang—during closing and knitting together of the slit faces. These and other lubricious and/or low-friction solutions are contemplated. Note that such coatings can be used with a variety of base materials that form the distal support segment and/or compliant segment. For instance, in one embodiment a parylene coating can be included on one or both the slit faces when the distal support segment, the compliant segment, or both components include polyurethane.

In addition, in one embodiment the lubricious or low-friction coating can be applied to the first slit face before the compliant segment is molded to the distal support segment. This enables the slit valve to be automatically defined by virtue of the two faces being unable to adhere to one another. In this and other embodiments herein, note that the force required to open the slit valve can vary according to various factors including friction between the slit faces, slit length, durometers of the compliant segment and distal support segment, valve wall thickness, etc.

FIGS. 5A and 5C show that the deformation region is further implemented in the present embodiment as a thinned portion 144 longitudinally centered on the slit valve 136 and disposed such that the thinnest portion thereof is adjacent to the second slit face 138B. Note that the longitudinal length of the thinned portion 144 is less than that of the slit 138, though the dimensions shown and described herein can vary. Indeed, the length, width, tapering, position, etc. of the thinned portion 144 can be modified as appreciated by one skilled in the art.

In the present embodiment, the deformation region including the compliant segment 140 and thinned portion 144 is configured to preferentially and bi-directionally deform near the slit valve 136 under pressure to open the slit 138, while the distal support segment 134 is less apt to deform. Indeed, during infusion of fluids through the catheter 22, the compliant segment 140 proximate the slit valve 136 deforms radially outward so as to enable fluids to pass out the lumen 143 of the catheter tube 22 through the slit 138. Correspondingly, during fluid aspiration, the compliant segment 140 proximate the slit valve 136 deforms radially inward so as to enable fluids to enter the lumen 143 of the catheter tube 22. Once infusion or aspiration forces are removed, the slit valve 136 resiliently returns to its rest state to re-seal the catheter tube lumen 143. Note that the deformation region just described above assists in preventing "hang up" of the first face 138A of the slit 138 against the second face 138B when the slit valve 136 returns to a closed position.

In another embodiment, it is appreciated that the thinned portion of the deformation region can thin from the outside of the catheter tube outer wall such that the inner diameter of the catheter tube lumen is uniformly smooth. Note that while the present discussion describes the valve assembly 130 as including a single lumen catheter, in other embodiments one or more lumens of a multi-lumen catheter tube may include valve assemblies as described herein. Note also that all or some of the deformation region, compliant segment, and/or distal support segment can be color-coded to indicate a certain aspect of the catheter, such as its ability to withstand pressures associated with power injection, for instance.

Figure 6A:
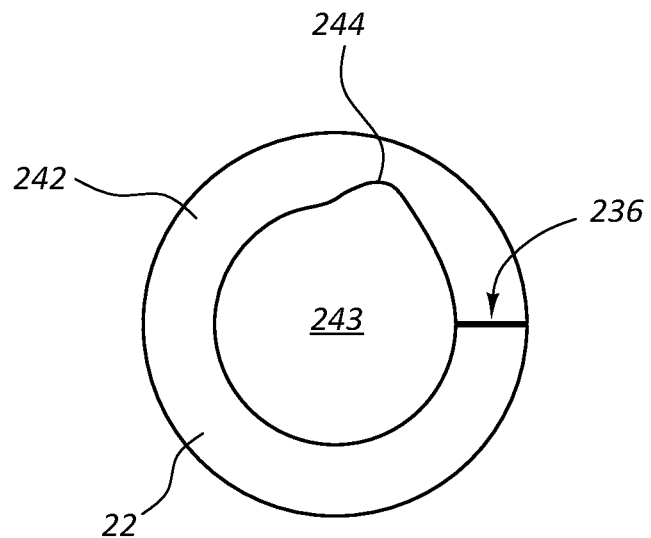
FIGS. 6A-6B show various cross sectional views showing operation of a distal valve of a catheter tube according to one embodiment.
Figure 6B:
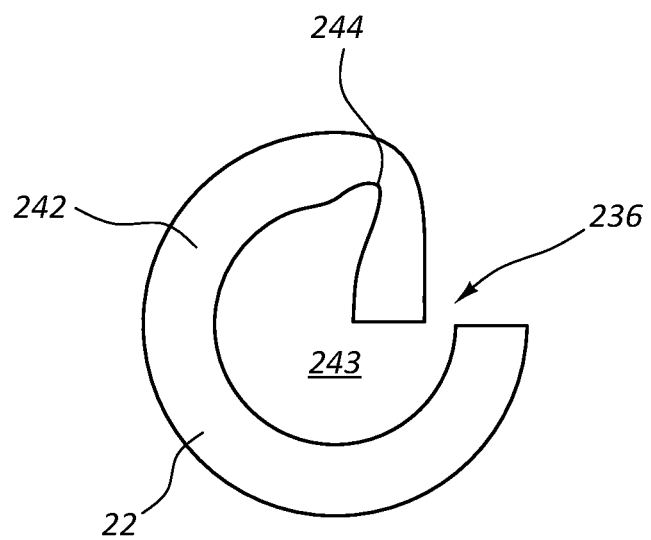

FIGS. 6A and 6B show the catheter tube 22 including a deformation region according to another embodiment, wherein a thinned portion 244 of an outer wall 242 of the catheter tube is disposed at a spaced apart location with respect to a slit valve 236. As shown, in FIG. 6B, the thinned portion 244 of the deformation region in the illustrated position assists in readily opening the slit valve 236 under an aspiration force. Thus, it is seen that the position of the thinned portion of the deformation region can be varied while still falling within the principles of the present embodiments.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A catheter, comprising:
   an outer wall circumscribing at least one lumen;
   a closed distal end;
   a distal segment adjacent the closed distal end;
   a slit valve extending through the outer wall in the distal segment; and
   a compliant segment forming a discrete portion of the outer wall in the distal segment, the compliant segment circumferentially spaced opposite of the slit valve to facilitate inward deflection of the distal segment along the slit valve when negative pressure is applied to the at least one lumen.

2. The catheter according to claim 1, wherein the compliant segment includes a lower material strength relative to surrounding portions of the outer wall in the distal segment.

3. The catheter according to claim 1, wherein the compliant segment is more compliant relative to surrounding portions of the outer wall in the distal segment.

4. The catheter according to claim 1, wherein the compliant segment includes a material possessing a second durometer less than a first durometer possessed by a material of the surrounding portions of the outer wall in the distal segment.

5. The catheter according to claim 4, wherein a durometer difference of about 20 exists between the first durometer and the second durometer.

6. The catheter according to claim 1, wherein the compliant segment has a length longer than a length of the slit valve.

7. The catheter according to claim 1, wherein the compliant segment includes a thinned portion having a thickness less than a thickness of surrounding portions of the outer wall in the distal segment.

8. The catheter according to claim 7, wherein the thinned portion tapers in a circumferential direction between a minimum thickness and a maximum thickness.

9. The catheter according to claim 8, wherein the minimum thickness of the thinned portion is disposed about 180 degrees from the slit valve.

10. The catheter according to claim 1, wherein the slit valve includes a length-to-width ratio of about 10 to 1, a width of the slit valve measured as a thickness of the outer wall.

11. The catheter according to claim 1, wherein a circumferential breadth of the compliant segment is about 25% of a circumference of the outer wall.

12. The catheter according to claim 1, wherein the catheter is formed of a material selected from the group consisting of silicone, polyurethane, polyurethane/silicone mixtures, polycarbonate/polyurethane copolymers, and combinations thereof.

13. The catheter according to claim 12, wherein the selected material is polyurethane, further comprising a parylene coating disposed on the slit valve.

14. The catheter according to claim 1, wherein a durometer rating for the compliant segment is about 10 to 20 less than a durometer rating for a portion of the outer wall surrounding the compliant segment.

* * * * *